United States Patent [19]
Weaver et al.

[11] Patent Number: 5,542,948
[45] Date of Patent: Aug. 6, 1996

[54] SURGICAL COMBINATION INJECT AND SNARE APPARATUS

[75] Inventors: George W. Weaver, East Earl, Pa.; Harold Jacob, Lawrence, N.Y.; Damond C. Holsinger, New Holland, Pa.

[73] Assignee: Arrow Precision Products, Inc., Pa.

[21] Appl. No.: 248,504

[22] Filed: May 24, 1994

[51] Int. Cl.[6] ................................................. A61B 17/00
[52] U.S. Cl. ............................ 606/113; 606/110; 606/47
[58] Field of Search ..................... 606/1, 205–211, 606/106, 110, 113, 114, 127, 37–40, 44–50, 108; 604/164, 264

[56] References Cited

U.S. PATENT DOCUMENTS

| | | | |
|---|---|---|---|
| 5,084,054 | 1/1992 | Bencini et al. | |
| 5,163,942 | 11/1992 | Rydell | 606/113 |
| 5,190,542 | 3/1993 | Nakao et al. | |
| 5,224,931 | 7/1993 | Kumar | 606/205 |
| 5,290,294 | 3/1994 | Cox et al. | 606/113 |
| 5,290,299 | 3/1994 | Fain et al. | 606/207 |
| 5,336,227 | 8/1994 | Nakao et al. | 606/110 |
| 5,376,094 | 12/1994 | Kline | 606/113 |
| 5,395,367 | 3/1995 | Wilk | 606/1 |

OTHER PUBLICATIONS

Gastrointestinal Endoscopy, "The Successive Strip Biopsy Partial Resection Technique For Large Early Gastric and Colon Cancers" Mikio Karita, MD, Masahiro Tada, MD Kiwamu Okita, MD, pp. 174–178, vol. 38, No. 2, 1992.
Gastrointestinal Endoscopy, "Endoscopic Therapy For Early Colon Cancer: The Strip Biopsy Resection Technique" Mikio Karita, MD, Masahiro Tada, MD, Kiwamu Okita MD pp. 128–132, vol. 37, No. 2, 1991.

*Primary Examiner*—Steven C. Pellegrino
*Assistant Examiner*—Glenn Dawson
*Attorney, Agent, or Firm*—Amster, Rothstein & Ebenstein

[57] ABSTRACT

A surgical apparatus for simultaneously deploying a first instrument while retrieving a second instrument from the distal end of a sheath and vice versa with a single stroke actuator. The actuator includes an elongated support having a provision for grasping at one end thereof, a first sliding member having provisions for grasping and which is movable in first and second directions relative to the support, and a second sliding member operably coupled to the first sliding member such that translation of the first and second sliding members is in opposite directions relative to the support. The first sliding member is connected to the first instrument and the second sliding member is connected to the second instrument.

8 Claims, 7 Drawing Sheets

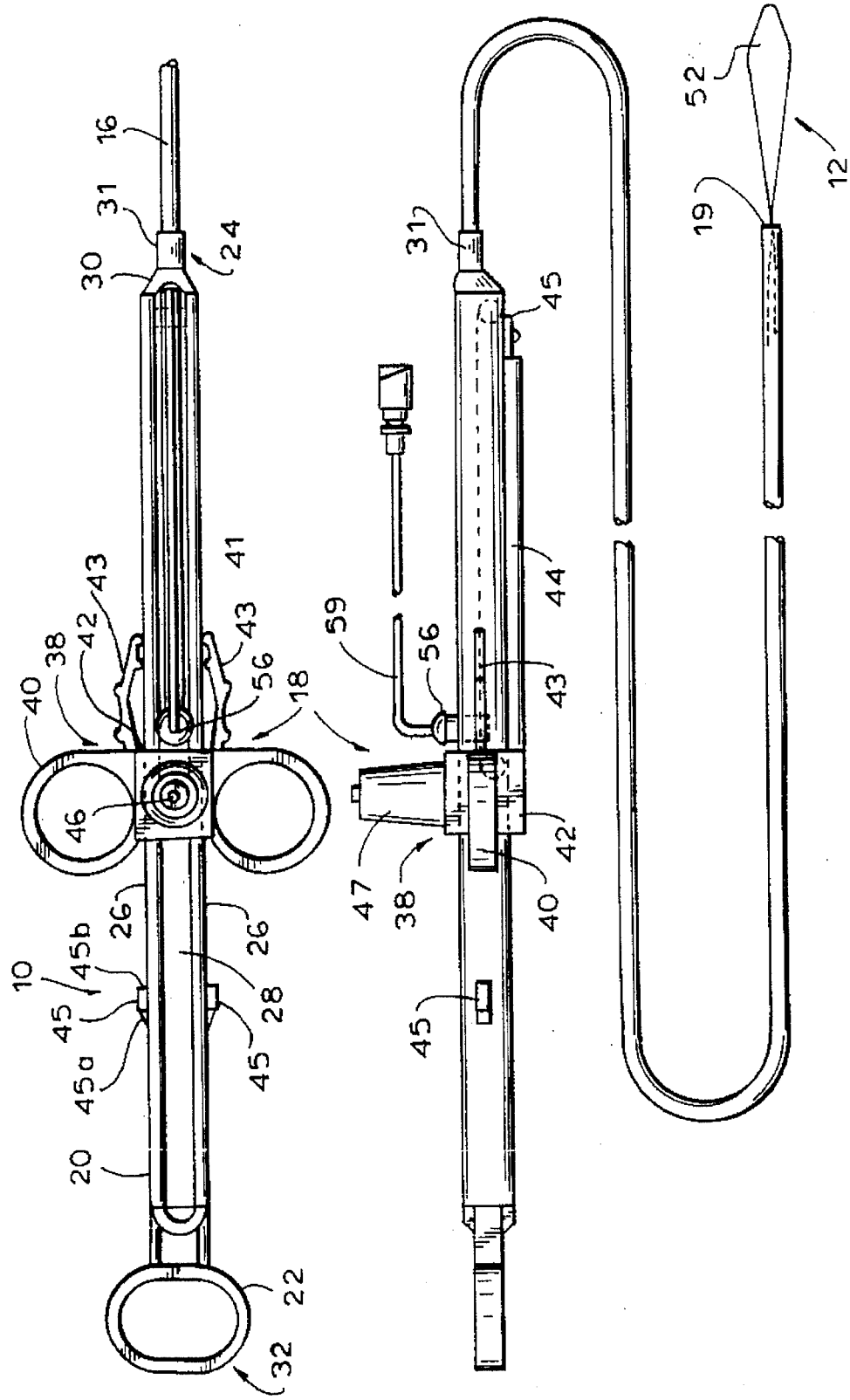

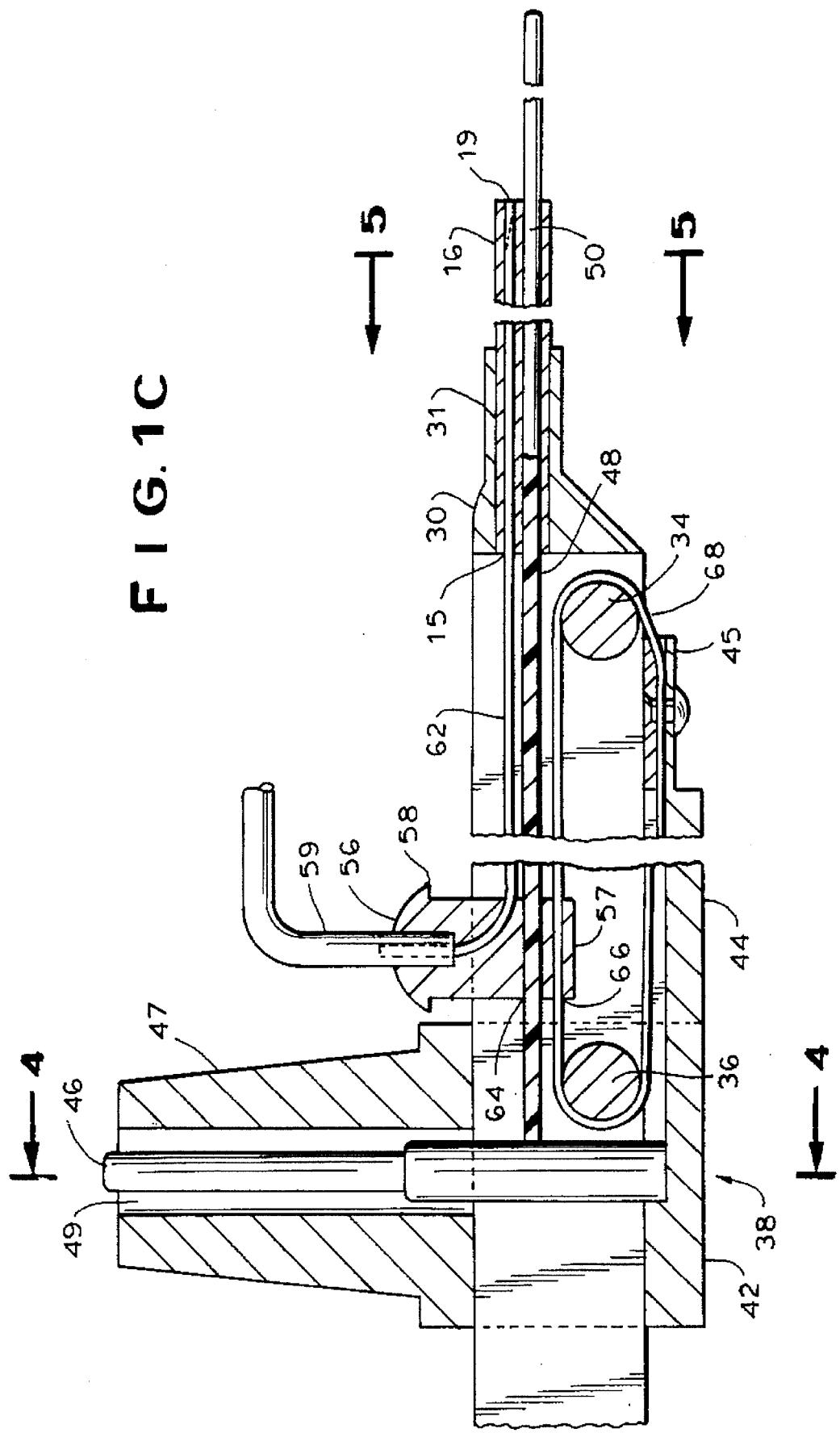

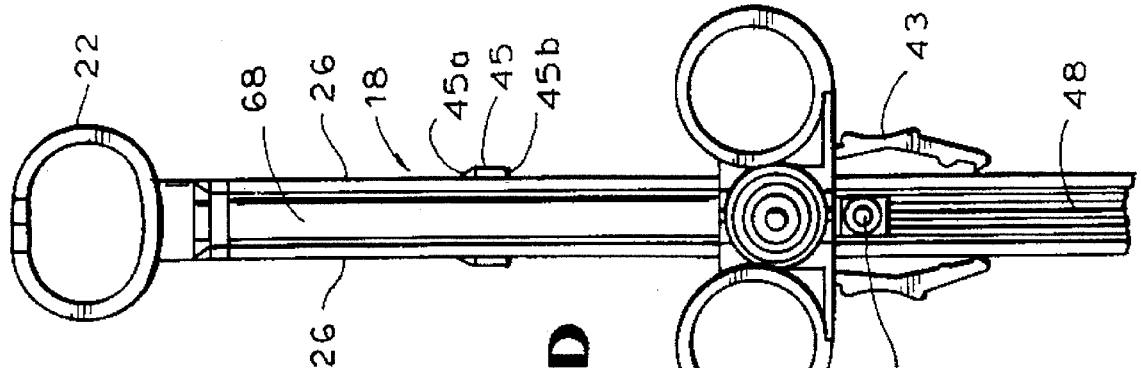
FIG. 1D
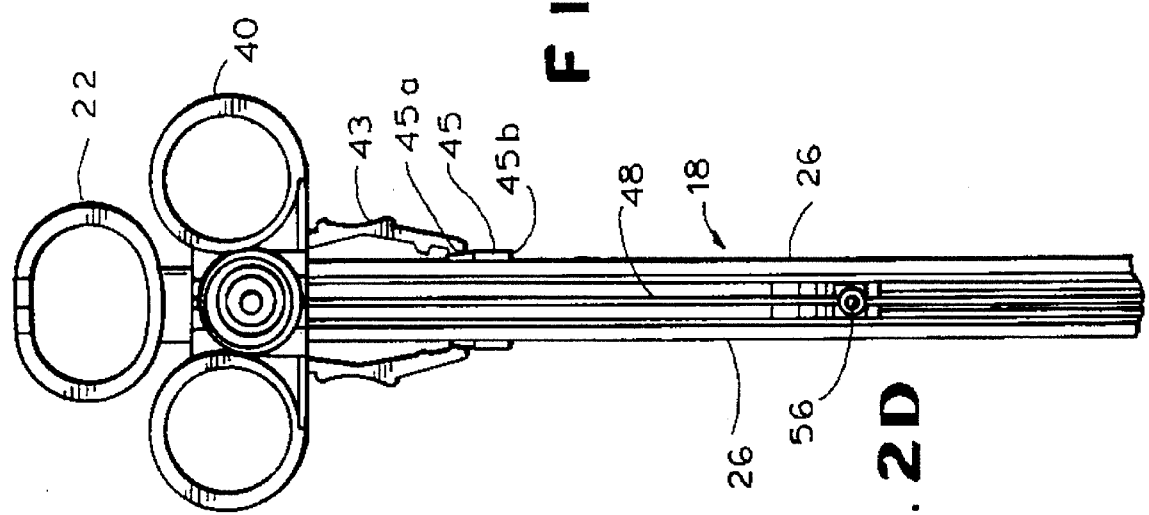
FIG. 3B
FIG. 2D
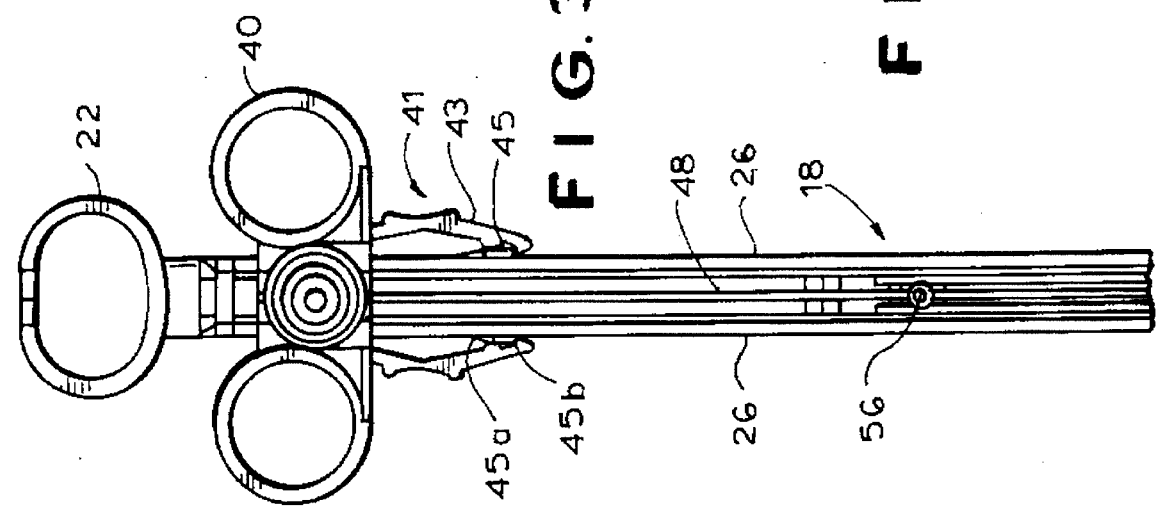

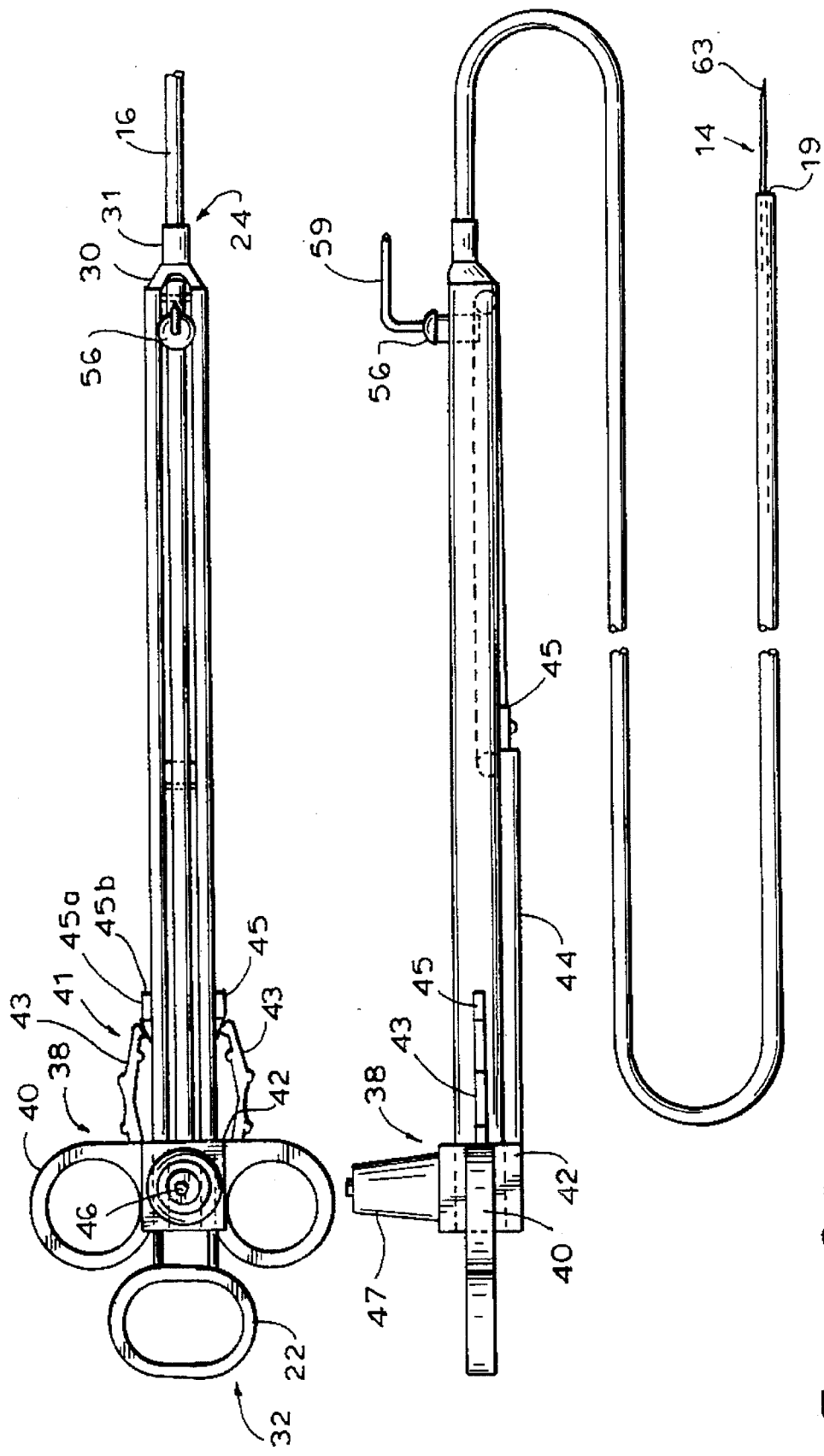

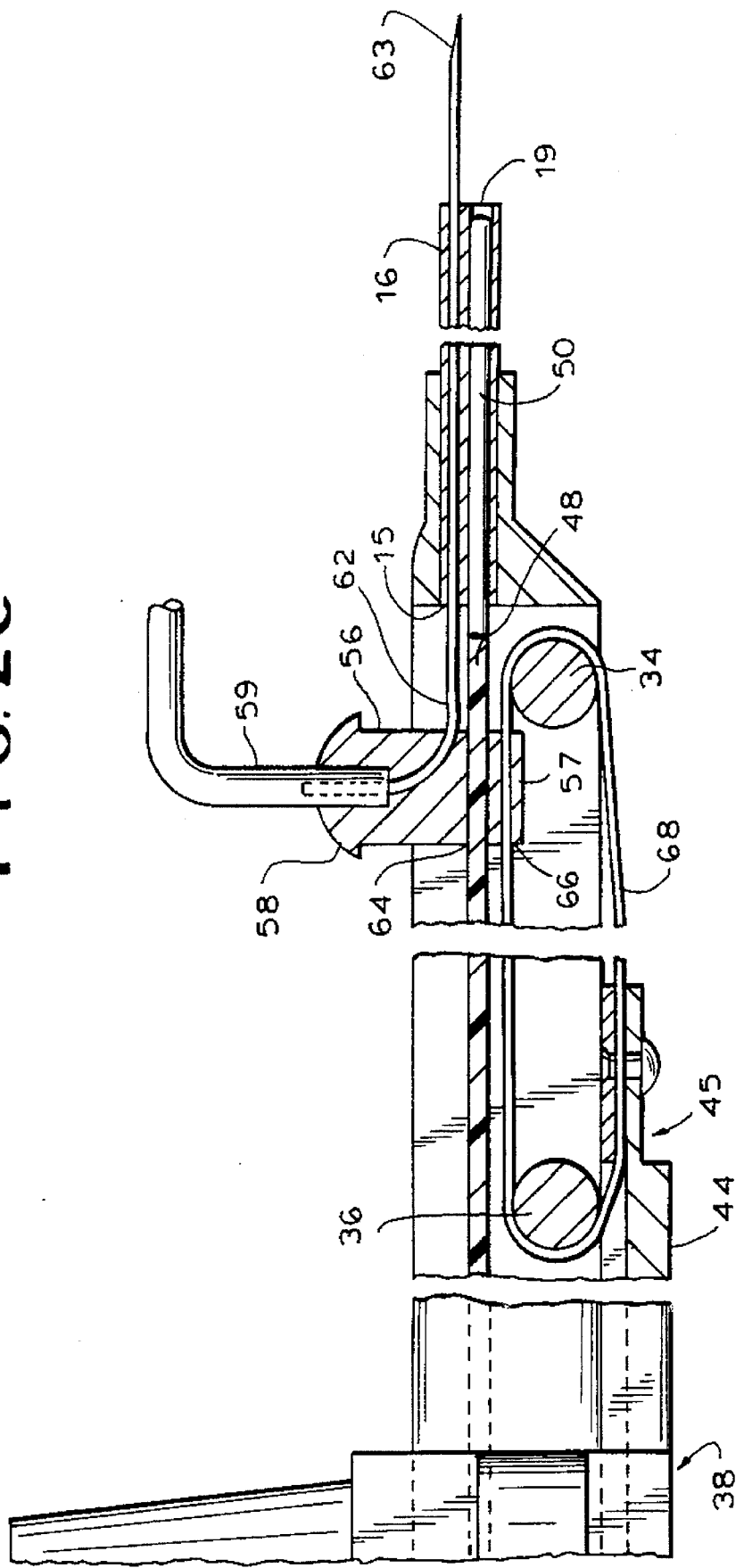

SURGICAL COMBINATION INJECT AND SNARE APPARATUS

FIELD OF THE INVENTION

This invention relates generally to an apparatus for simultaneously deploying a first instrument and retrieving a second instrument, respectively, with a single-stroke actuator, and more particularly to a surgical apparatus for performing endoscopic procedures such as biopsy or polyp resection and the like (also known as endoscopic polypectomy).

DESCRIPTION OF THE PRIOR ART

A technique developed in Japan known as Strip Biopsy Resection or Saline-Assisted Polypectomy ("SAP") enables physicians to easily remove sessile and other morphological type lesions of the gastrointestinal tract. SAP involves elevating the lesion on a bed of physiological saline solution, and then passing a standard snare device over the elevated tissue to resect the same by electrocoagulation. In the course of performing this procedure, the physician passes a sheath having an injection needle disposed therein through an endoscope, the distal end of which is proximate to the site of the lesion within the gastrointestinal tract of the patient. The needle is then moved out of the sheath and inserted into the submucosa proximal to the lesion. A sufficient amount of saline solution is then injected into the submucosa to elevate the lesion. Once the lesion is elevated, the needle is then withdrawn into the sheath and the sheath and needle are removed from the endoscope and replaced with a snare or cauterization loop contained in a separate sheath. The snare is placed over the lesion and the overlying mucosa, tightened, and the lesion is then separated from the surrounding tissue electro-surgically. The same technique may be applied to depressed lesions as well as sessile polyps, regardless of their size.

After excision of the lesion, it is often necessary to inject a cold epinephrine solution in order to curtail any bleeding that often arises after the excision. This is critical since bleeding must be stopped as soon as it starts to avoid complications from the procedure which could have adverse effects on the patient. It is therefore desirable to have the injection needle ready for quick redeployment at the site after excision of the lesion.

The foregoing endoscopic procedures can also be used for marking the location of a lesion or resected polyp by introducing an injection needle either before or after the use of a polypectomy snare. A diluted solution of sterilized India ink is injected into four quadrants around the colon to permit surgical identification of the site. In this manner, the physician can monitor the patient endoscopically for a predetermined amount of time until complete healing of the site has been identified or various points of interest can be marked for future endoscopic identification.

Surgical instruments for use in such procedures are disclosed in U.S. Pat. Nos. 5,190,542 to Nakao, et al. and 5,084,054 to Bencini et al. Both patents teach the use of surgical gripping instruments which facilitate the remote manipulation of an endoscopically inserted snare or cauterization loop disposed at the distal end of a sheath. Common to both disclosures is the teaching of a sliding member coupled to a support assembly which allows the physician to manipulate the snare by moving the sliding member relative to the support assembly to deploy or retrieve the snare from the sheath.

These devices have disadvantages. Since the Nakao and Bencini inventions can only manipulate one remote instrument at a time, the procedure time is unnecessarily increased because the physician must continually swap the snare and injection needle devices to perform the various injection and resection steps of the biopsy process. Having an injection needle continually present at the site would make such colonscopic procedures easier, more convenient and less time consuming for the physician and patient. More importantly, in the case of sudden and severe bleeding complications, epinephrine could be delivered without having to insert through the endoscope or manipulate a separate device.

As such, a need exists for a device which allows locating both the injection needle and the snare simultaneously at the site of the lesion. However, such a device should not permit the deployment of the injection needle until the snare is completely withdrawn and vice versa. This is necessary to prevent complications that can arise if both instruments are accidentally deployed simultaneously. Specifically, an accidental perforation with a "hot" injection needle can short-out the conductive path of the snare. Also, the snare wire and injection needle can become entangled.

In view of the aforementioned shortcomings in the prior art, it is an object of the present invention to provide a surgical apparatus for simultaneously deploying a first instrument and retrieving a second instrument, respectively, by manipulating a single actuator assembly.

It is another object of the present invention to provide a surgical apparatus for deploying a first instrument and retrieving a second instrument, respectively, wherein a locking mechanism prevents inadvertent deployment and retrieval of at least one of the first and second instruments, respectively.

It is a further object of the present invention to provide a surgical apparatus for deploying and retrieving an injection needle and a snare for electrocautery in endoscopic procedures.

It is yet another object of the present invention to provide a surgical apparatus where a first medical instrument is deployed while a second medical instrument is simultaneously retrieved and vice versa from an elongated sheathing member with a single-stroke actuator assembly.

It is still another object of the present invention to provide a combination inject and snare device for use in endoscopic procedures where the simultaneous, opposite deployment and retrieval of an injection needle and a snare prevents undesirable complications which can arise from the injection needle short-circuiting the conductive path of, or becoming entangled with the snare.

It is still another object of the present invention to provide a combination inject and snare device for use in endoscopic procedures which eliminates the need for relocating the lesion or polyp when going from one procedure (e.g., injection of polyp) to another (e.g., separation of the polyp).

It is still another object of the present invention to provide a surgical apparatus for use in endoscopic procedures where an injection needle and snare are simultaneously present near the site of the procedure while disposed at the distal end of the device for independent deployment and retrieval by the physician.

It is still another object of the present invention to provide an apparatus for simultaneously deploying a first instrument and retrieving a second instrument, respectively, in which a first sliding member disposed in a support member is operably coupled to a second sliding member to facilitate simultaneous opposite travel of the first and second instruments relative to the distal end of an elongated sheath.

SUMMARY OF THE INVENTION

In accordance with the above objects of the invention and additional objects which will become apparent hereinafter, the present invention provides an apparatus generally comprised of a first instrument (e.g., a snare for electrocautery) extendable in a first direction and retractable in a second direction; a second instrument (e.g., an injection needle) extendable in the first direction when the first instrument is retracted in the second direction, and retractable in the second direction when the first instrument is extended in the first direction; a sheath, either elongated or truncated, for the first and second instruments, the sheath having a distal end if elongated for remote procedures; a support structure having integral provisions for grasping by one of the user's fingers, such as the thumb; a first slide having provisions for grasping thereof, such as a pair of finger rings, where the first slide is slidably connected to the support for movement in the first direction and the second direction relative thereto and connected to at least one of the first instrument and the second instrument; and a second slide for enabling movement of the first instrument and the second instrument in opposite directions, where the first and second slides, respectively, are operably connected by an elongated endless belt having at least first and second axels affixed relative to the support, and the endless belt is attached to both the first and second slides, respectively, for causing the second slide to move in an opposite direction relative to the first slide when the first slide is translated relative to the support.

The support is generally an elongated structure having a pair of opposed rails which define a central channel and terminate at one end in a thumb-ring for grasping, and a tapered front portion at the opposite end for receiving an elongated sheath.

In one embodiment of the invention, the sheath includes a distal end remotely disposed from the support for guiding the first and second instruments to a remote site, such as in colonscopic procedures. The sheath includes a plurality of lumens for receiving the first and second instruments as well as for receiving additional accessories which may be required to perform the procedure, such as an observation element or guidewire. The lumens serve to insulate the instruments from each other to prevent short circuiting if a snare is used for electrocauterization.

The first slide includes a pair of finger-rings for grasping, integrally formed with or attached to a hub which is slidably disposed on the support. The first slide is movable relative to the support towards and away from the respective ends thereof by grasping the thumb-ring with the thumb, and the finger-rings on the first slide with the forefinger and index finger. A connector attached to the hub communicates electrically with a wire coupled to the snare for attachment to an external power source, instrument or measuring device.

The second slide is slidably disposed within the channel of the support to facilitate deployment and retrieval of the second instrument in conjunction with the respective retrieval and deployment of the first instrument by moving the first slide relative to the support. The second slide is coupled to an endless belt which is positioned about the first and second axels within the channel of the support such that a single stroke of the first slide relative to the support effectuates the respective simultaneous deployment of the first instrument and retrieval of the second instrument relative to the distal end of the sheath. As an option, a locking means may be incorporated into the device to prevent inadvertent deployment of the injection needle during the procedure. In the preferred embodiment, the locking means maintains the first slide in a neutral position where both the snare and injection needle are retracted within the sheath.

BRIEF DESCRIPTION OF THE DRAWINGS

FIG. 1A is a partial top plan view of the surgical apparatus with the first slide in the fully extended position to deploy the loop-snare, and the second slide in the fully retracted position to retrieve the injection needle;

FIG. 1B is a side elevational view of the surgical apparatus with the first slide in the fully extended position to deploy the loop-snare, and the second slide in the fully retracted position to retrieve the injection needle;

FIG. 1C is a partial sectional view of the surgical apparatus depicting the deployment/retrieval mechanism when the loop-snare is deployed;

FIG. 1D is an enlarged partial top plan view of the surgical apparatus in the fully extended position to deploy the loop-snare showing the first slide in the snare position;

FIG. 2A is a partial top plan view of the surgical apparatus with the first slide in the fully retracted position to retrieve the loop-snare, and the second slide in the fully extended position to deploy the injection needle;

FIG. 2B is a side elevational view of the surgical apparatus with the first slide in the fully retracted position to retrieve the loop-snare, and the second slide in the fully extended position to deploy the injection needle;

FIG. 2C is a partial sectional view depicting the deployment/retrieval mechanism when the injection needle is deployed;

FIG. 2D is an enlarged partial top plan view of the surgical apparatus with the first slide in the fully retracted position to retrieve the loop-snare and deploy the injection needle;

FIG. 3B is an enlarged partial top plan view of the surgical apparatus with the first slide maintained in the neutral position by the locking mechanism where both the loop-snare and injection needle are maintained in a retracted position within the sheath;

DETAILED DESCRIPTION OF THE PREFERRED EMBODIMENT

Figure 3A:
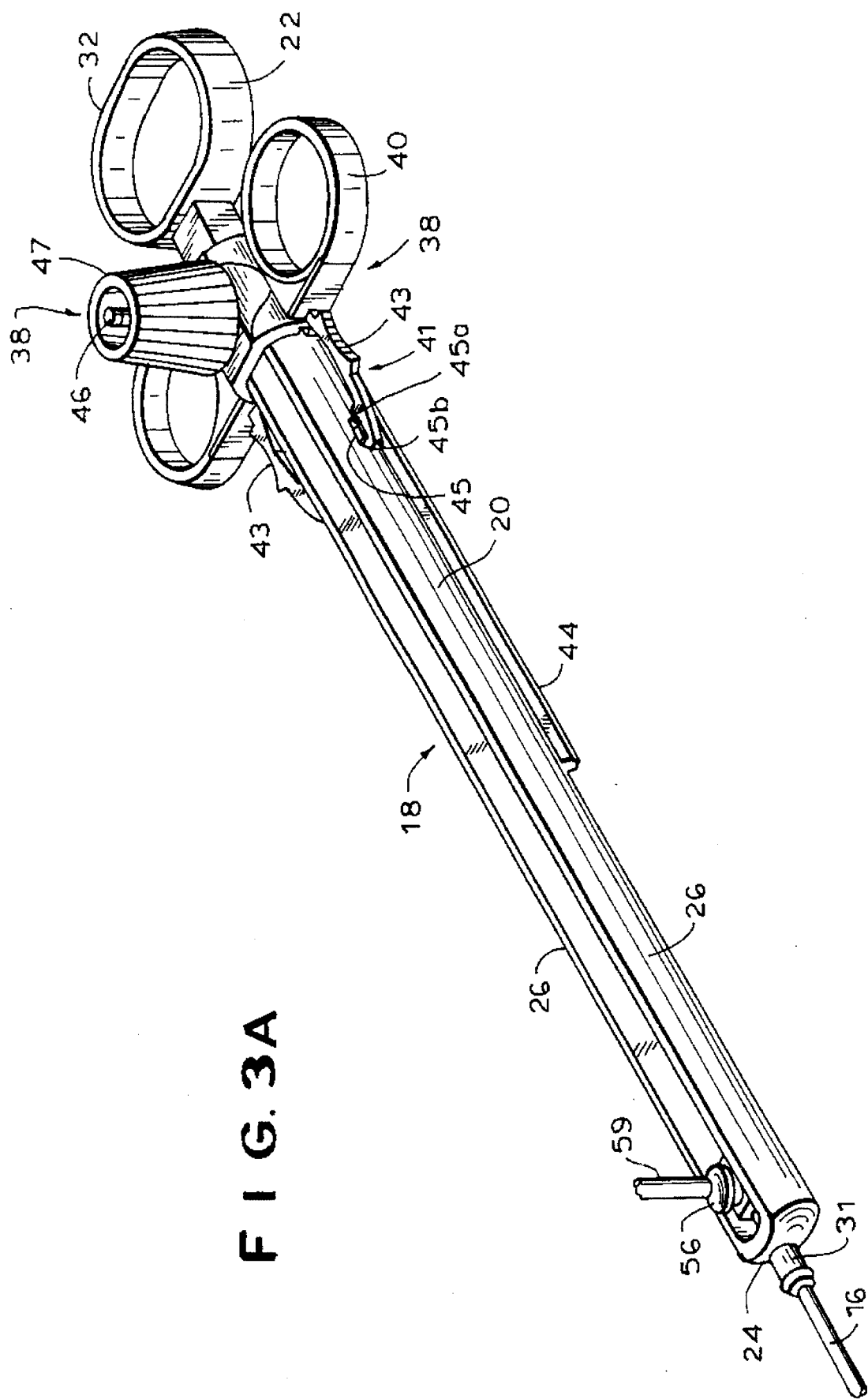
FIG. 3A is an isometric view of the surgical apparatus with the first slide in the neutral position where both the loop-snare and injection needle are maintained in a retracted position within the sheath.

With reference to the several views of the drawings, there is provided a surgical apparatus generally characterized by the reference numeral 10 for deploying and retrieving a first instrument 12 and a second instrument 14 from an elongated sheath 16 by manipulating an actuator assembly 18.

Referring now to FIGS. 1A–1D, 2A–2D, and 3A, 3B, actuator assembly 18 comprises a support 20 fabricated from a plastic material such as polycarbonate, defined by a first end 24 and a second end 32. A thumb-ring 22 is disposed at or proximal to the second end 32 to facilitate grasping. Support 20 is generally an elongated structure having a pair of opposed rails 26 which define a central channel 28. Rails 26 and channel 28 terminate in a front portion 30 at the first end 24. Front portion 30 includes a tapered extension 31 having a hollow bore extending therethrough for attaching sheath 16 to the support. As shown in FIGS. 1C and 2C, a first axle 34 is disposed within channel 28 and transversely positioned near front portion 30. A second axle 36 is disposed within channel 28 and transversely positioned rearwardly toward the second end 32 relative to the first axle 34.

Figure 5:
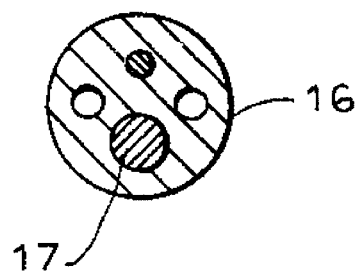
FIG. 5 is a sectional view along lines 5—5 of FIG. 1C.

Sheath 16 is defined by a proximal end 15 and a distal end 19. Sheath 16 is preferably fabricated from a flexible material such as teflon and includes a plurality of lumens 17 for connecting the first and second instruments 12, 14, respectively to the actuator assembly 18, and for connecting other accessories as required (not shown). As depicted in FIG. 5, the lumens 17 are appropriately sized to receive the respective instruments and any accessories therein. If there are only two instruments for use with the apparatus, sheath 16 may or may not have additional lumens which serve no functional purpose. In the exemplary embodiment, the first and second instruments are an injection needle and loop-snare for use in, for example, a polypectomy inject and snare or like procedure.

A first slide 38 for deploying and retrieving the first instrument 12 is slidably connected to support 20. The first slide 38 includes a pair of finger rings 40 for grasping by the user, which may be integrally formed with hub 42. An elongated tongue 44 integral with hub 42 and having a distal end 45 extends longitudinally beneath the rails 26 of support 20. The first slide 38 is movable relative to support 20 towards and away from the respective first and second ends 24 and 32 thereof by grasping finger ring 22 with the thumb and finger rings 40 with the forefinger and index finger.

To prevent inadvertent deployment of either of the first instrument 12 (e.g., the loop-snare 52) or the second instrument 14 (e.g., the injection needle 63), a locking mechanism 41 includes a pair of flexible fingers 43 having detents which project from the first slide 38 and interlock with tabs 45 disposed and projecting outwardly from the rails 26 of support 20. This arrangement prevents the first slide 38 from being accidentally moved relative to the support 20 without first applying finger pressure to the flexible fingers 43 to disengage the same from the tabs 45. In the illustrative embodiment, the tabs 45 are each provided with a tapered surface 45a where such taper allows the first slide 38 to be translated forwardly into the SNARE POSITION (FIGS. 1A-1D), to deploy the loop-snare 52 without having to manually depress the flexible fingers 43. Because the opposite side of tab 45 has a non-tapered surface 45b, the first slide 38 is prevented from being pulled rearwardly past the NEUTRAL POSITION (FIGS. 3A, 3B) and into the INJECTION NEEDLE POSITION (FIGS. 2A-2D), so as to prevent inadvertent deployment of the injection needle 63.

Of course, it is contemplated that tab 45 may be provided with identical non-tapered opposed surfaces 45b to prevent any movement of the first slide 38 from the neutral position (FIGS. 3A, 3B). Thus, any deployment or retrieval of either instrument would require that the user manually depress the flexible fingers 43.

Figure 4:
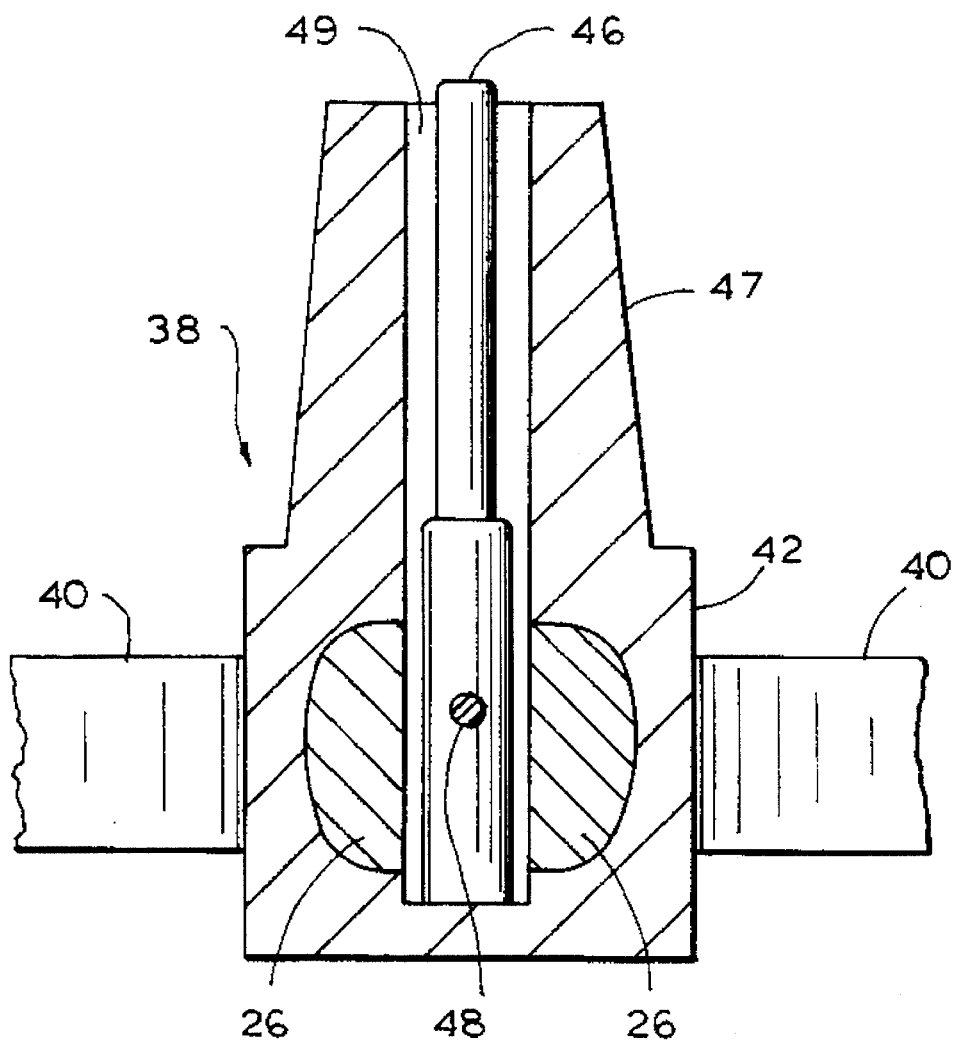
FIG. 4 is a sectional view along lines 4—4 of FIG. 1C.

As shown in FIG. 4, a connector 46 fabricated from electrically conductive material is disposed within and attached to hub 42 and extends upwardly to facilitate attachment to an external power source, instrument or measuring device (not shown). An insulative cap 47 is attached to hub 42 and includes a hollow bore 49 to provide access to connector 46. An elongated rod 48 is attached to and in electrical contact with connector 46 at one end thereof and attached to a flexible wire 50 at the opposite end thereof. Flexible wire 50 extends through a lumen 17 of sheath 16 and includes a loop-snare 52 (i.e., the first instrument 12) at the distal end thereof. Loop-snare 52 may be attached to wire 50 by a swagged sleeve (not shown) or by other conventional methods.

A second slide 56 is slidably disposed within channel 28 of support 20 to facilitate deployment and retrieval of an injection needle 63 (i.e., the second instrument 14) in conjunction with the respective retrieval and deployment of the loop-snare 52 by moving the first slide 38 relative to support 20. The second slide 56 includes a bulbous head 58 which receives an injection needle extension line 59 which in turn is coupled to an injection needle sleeve 62. The injection needle sleeve 62 extends through a lumen 17 of sheath 16 where it is connected to injection needle 63 at its distal end. A first aperture 64 extending through the second slide 56 permits rod 48 to pass therethrough and move independently, i.e., in a direction of travel opposite that of the second slide 56. In this manner, rod 48 can move in a first direction of travel while the second slide 56 simultaneously moves in a second direction and vice versa. A second aperture 66 permits an endless belt 68 to pass through and connect to the second slide 56 to facilitate movement thereof. Alternatively, endless belt 68 could be fastened or attached to the second slide 56 by other means, such as directly to the bottom surface 57 thereof in lieu of passing through aperture 66.

Endless belt 68 is supported by the first axle 34 and the second axle 36 within channel 28 and attached to the distal end 45 of tongue 44. In this manner, as shown in FIGS. 1A-1C, when the first slide 38 is translated relative to support 20 towards the first end 24 thereof, wire 50 and attached loop-snare 52 move in a first direction relative to the distal end 19 of sheath 16 for deployment therefrom. Simultaneously, tongue 44 of the first slide 38 causes endless belt 68 to move the second slide 56 in a second direction (i.e., rearwardly towards the second end 32 of support 20), thereby retrieving injection needle 63 until it is disposed entirely within its lumen 17 of sheath 16. Conversely, as shown in FIGS. 2A-2C, when the first slide 38 is translated towards the second end 32 (the end containing finger end 22), rod 48, wire 50 and the attached loop-snare 52 move in the second direction to retrieve the loop-snare 52 for storage entirely within its lumen 17 of sheath 16. At the same time, tongue 44 of the first slide 38 travels in the same direction (the second direction) to cause endless belt 68 to move the second slide 56 in the first direction to ultimately deploy injection needle 63 from the distal end 19 of sheath 16.

In view of the foregoing description of the invention, it will be appreciated that a single stroke of the first slide 38 relative to the support 20 effectuates the respective simultaneous deployment of the first instrument 12 and retrieval of the second instrument 14. Although the exemplary embodiment of the invention which is described and illustrated herein relates to an apparatus to facilitate the deployment and retrieval of an injection needle and snare used in endoscopic procedures such as polypectomy injection, snare and retrieval, it is anticipated that an apparatus in accordance with the invention might have many other applications where it is desirable to simultaneously deploy one structure while retrieving a second structure, regardless of whether the independent structures are remotely attached to the device by elongated provisions such as those shown and described. In this regard, certain applications may only necessitate that the first and second instruments 12, 14 be deployed and retrieved from the support 20 which itself functions as the sheath, where the remote application of the instruments is not required (e.g., a device for providing multiple injections or the like) or in other medical applications requiring the simultaneous deployment and retrieval of separate structures.

The present invention has been shown and described in what is considered to be the most practical and preferred embodiment. It is anticipated, however, that departures may be made therefrom and that obvious modifications will occur to persons skilled in the art.

We claim:

1. An apparatus comprising:

a first instrument including an injection needle;

a second instrument including a snare;

sheathing means for sheathing said first and second instruments, said sheathing means having a proximal end and a distal end; and actuator means for simultaneously extending said first instrument relative to said distal end of said sheathing means in a first direction and retracting said second instrument in a second direction relative to said distal end of said sheathing means, and for simultaneously extending said second instrument relative to said distal end of said sheathing means in said first direction and retracting said first instrument in said second direction relative to said distal end of said sheathing means.

2. The surgical apparatus recited in claim 1, wherein said actuator means comprises:

a support having means for grasping thereof;

a handle having means for grasping thereof, said handle slidably connected to said support for movement in said first direction and said second direction relative thereto and connected to at least one of said first instrument and said second instrument; and slide means for enabling movement of said first instrument and said second instrument in opposite directions, said slide means movable with respect to said support and operably connected to said handle.

3. The surgical apparatus recited in claim 2, wherein said operable connection between said slide means and said handle comprises an elongated endless belt and at least first and second axles affixed relative to said support, said endless belt being disposed about said axles and attached to said slide means and attached to said handle for causing said slide means to move in said first and second directions relative to said support.

4. An apparatus, comprising:

a first instrument;

a second instrument;

sheathing means for sheathing said first and second instruments, said sheathing means having a proximal end and a distal end; and actuator means for simultaneously extending said first instrument relative to said distal end of said sheathing means in a first direction and retracting said second instrument in a second direction relative to said distal end of said sheathing means, and for simultaneously extending said second instrument relative to said distal end of said sheathing means in said first direction and retracting said first instrument in said second direction relative to said distal end of said sheathing means; and locking means for maintaining at least one of said first and second instruments in a retracted position within said sheathing means, said locking means requiring manual manipulation thereof to facilitate extension and retracting of said at least one of said first and second instruments relative to said sheathing means.

5. A surgical apparatus, comprising:

a needle attached to an elongated extension line for communicating fluids to and from said needle, said needle being extendable in a first direction and retractable in a second direction;

a snare attached to an elongated extension line and extendable in said first direction when said needle is retracted in said second direction and retractable in said second direction when said needle is extended in said first direction;

sheathing means for sheathing said needle, said snare and said extension lines, said sheathing means having a proximal and a distal end; and actuator means for simultaneously extending said needle in said first direction and retracting said snare in said second direction, relative to said distal end of said sheathing means.

6. A surgical apparatus, comprising:

a needle attached to an elongated extension line for communicating fluids to and from said needle, said needle being extendable in a first direction and retractable in a second direction;

a snare attached to an elongated extension line and extendable in said first direction when said needle is retracted in said second direction and retractable in said second direction when said needle is extended in said first direction;

sheathing means for sheathing said needle, said snare and said extension lines, said sheathing means having a proximal and a distal end; and actuator means for extending said needle in said first direction and retracting said snare in said second direction, relative to said distal end of said sheathing means; said actuator means including:

a support having means for grasping thereof;

a first slide slidably connected to said support for movement in said first direction and said second direction relative thereto and connected to at least one of said needle and said snare; and a second slide for enabling movement of said needle and said snare in opposite directions, said second slide being movable with respect to said support and operably connected to said first slide.

7. A surgical apparatus, comprising:

a first instrument extendable in a first direction and retractable in a second direction;

a second instrument extendable in said first direction as said first instrument is being retracted in said second direction and retractable in said second direction as said first instrument is being extended in said first direction;

sheathing means for sheathing said first and second instruments, said sheathing means having a proximal end and a distal end;

a support having means for grasping thereof, said support and said sheathing means being secured together for movement as a unit;

a handle having means for grasping thereof, said handle being slidably connected to said support for movement in a first direction and a second direction relative thereto and connected to at least one of said first instrument and said second instrument; and slide means for enabling movement of said first instrument and said second instrument in opposite directions, said slide means being movable with respect to said support and operably connected to said handle.

8. An apparatus comprising:

a first instrument;

a second instrument;

sheathing means for sheathing said first and second instruments, said sheathing means having a proximal end and a distal end; and actuator means for simultaneously extending said first instrument relative to said distal end of said sheathing means in a first direction and retracting said second instrument in a second direction relative to said distal end of said sheathing means, and for simultaneously extending said second instrument relative to said distal end of said sheathing means in said first direction and retracting said first instrument in said second direction relative to said distal end of said sheathing means;

said sheathing means and said actuator means being secured together for movement as a unit.

* * * * *